US00PP37820P2

(12) United States Plant Patent
Yamada et al.

(10) Patent No.: US PP37,820 P2
(45) Date of Patent: Oct. 27, 2026

(54) ***MANDEVILLA* PLANT NAMED 'Sunpa 424'**

(50) Latin Name: *Mandevilla hybrida*
Varietal Denomination: SUNPA 424

(71) Applicants: Masahiro Yamada, Higashiomi (JP); Tomoya Misato, Higashiomi (JP)

(72) Inventors: Masahiro Yamada, Higashiomi (JP); Tomoya Misato, Higashiomi (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 19/342,319

(22) Filed: Sep. 26, 2025

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
CPC ..... A01H 5/02; A01H 5/00; A01H 6/08808
See application file for complete search history.

(56) References Cited

PUBLICATIONS

Grower Talks #CAST2025 Day 2: Nine Companies!, retrieved on Jan. 13, 2026 at https://www.growertalks.com/Newsletts/View/?article=4866, 24 pp. (Year: 2025).*
Suntory Flowers 2026 Catalog retrieved on Jan. 13, 2026 at https://suntoryflowers.com/catalog/, pp. 1-3, 12 (Year: 2026).*

* cited by examiner

*Primary Examiner* — June Hwu
(74) *Attorney, Agent, or Firm* — C. Anne Whealy

(57) ABSTRACT

A new and distinct cultivar of *Mandevilla* plant named 'Sunpa 424', characterized by its climbing plant habit; vigorous growth habit; freely branching habit; freely flowering habit; long flowering period; medium-sized purplish red-colored flowers; and good garden performance.

2 Drawing Sheets

Figure 1:
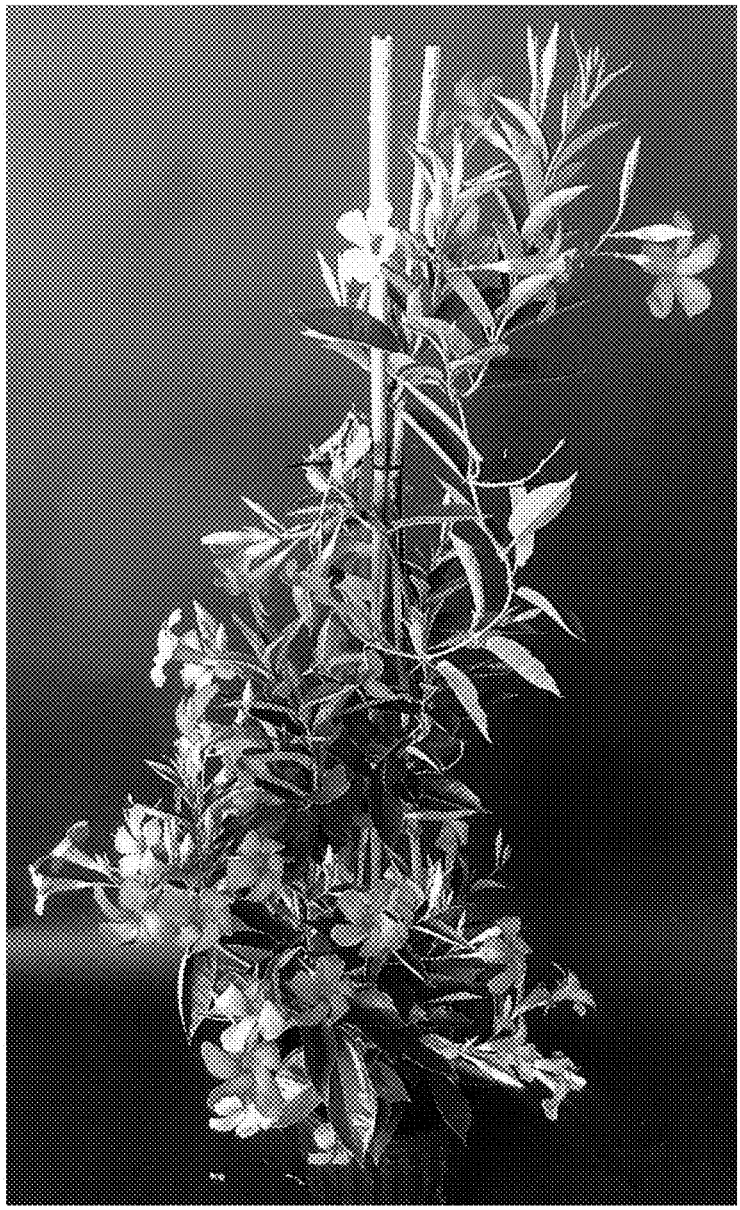

Botanical designation: *Mandevilla hybrida.*
Cultivar denomination: 'SUNPA 424'.

BACKGROUND OF THE INVENTION

The present invention relates to a new and distinct cultivar of *Mandevilla* plant, botanically known as *Mandevilla hybrida* and hereinafter referred to by the name 'Sunpa 424'.

The new *Mandevilla* plant is a product of a planned breeding program conducted by the Inventors in Higashiomi, Shiga, Japan. The objective of the breeding program is to develop new *Mandevilla* plants with a climbing plant habit and numerous pink-colored flowers.

The new *Mandevilla* plant originated from a cross-pollination by the Inventors in May, 2015 in Higashiomi, Shiga, Japan of a proprietary selection of *Mandevilla hybrida* identified as code number 12M162, not patented, as the female, or seed, parent with a proprietary selection of *Mandevilla hybrida* identified as code number 10M490, not patented, as the male, or pollen, parent. The new *Mandevilla* plant was discovered and selected by the Inventors as a single flowering plant from within the progeny of the stated cross-pollination grown in a controlled greenhouse environment in Higashiomi, Shiga, Japan in September, 2018.

Asexual reproduction of the new *Mandevilla* plant by terminal vegetative cuttings in Higashiomi, Shiga, Japan since March, 2019 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpa 424'. These characteristics in combination distinguish 'Sunpa 424' as a new and distinct *Mandevilla* plant:

1. Climbing plant habit.
2. Vigorous growth habit.
3. Freely branching habit.
4. Freely flowering habit.
5. Long flowering period.
6. Medium-sized purplish red-colored flowers.
7. Good garden performance.

Plants of the new *Mandevilla* can be compared to plants of the female selection parent. Plants of the new *Mandevilla* differ primarily from plants of the female parent selection in the following characteristics:

1. Plants of the new *Mandevilla* have longer leaves than plants of the female parent selection.
2. Plants of the new *Mandevilla* have larger flowers than plants of the female parent selection.

Plants of the new *Mandevilla* can be compared to plants of the male selection parent. Plants of the new *Mandevilla* differ primarily from plants of the male parent selection in the following characteristics:

1. Plants of the new *Mandevilla* have shorter leaves than plants of the male parent selection.
2. Plants of the new *Mandevilla* have smaller flowers than plants of the male parent selection.

Plants of the new *Mandevilla* can be compared to plants of the *Mandevilla hybrida* 'Sunparaprero', disclosed in U.S. Plant Pat. No. 19,399. In side-by-side comparisons, plants of the new *Mandevilla* differ from plants of 'Sunparaprero' in the following characteristics:

1. Plants of the new *Mandevilla* have shorter internodes than plants of 'Sunparaprero'.
2. Leaf arrangement of plants of the new *Mandevilla* is decussate whereas leaf arrangement of plants of 'Sunparaprero' is opposite.
3. Plants of the new *Mandevilla* have longer leaves than plants of 'Sunparaprero'.
4. Plants of the new *Mandevilla* have smaller flowers than plants of 'Sunparaprero'.
5. Flower petals of plants of the new *Mandevilla* are free and not imbricate whereas flower petals of plants of 'Sunparaprero' are imbricate.
6. Flower petals of plants of the new *Mandevilla* are purplish red in color whereas flower petals of plants of 'Sunparaprero' are dark purplish pink in color.
7. Plants of the new *Mandevilla* have shorter peduncles than plants of 'Sunparaprero'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'Sunpa 424' grown in a container.

Figure 2:
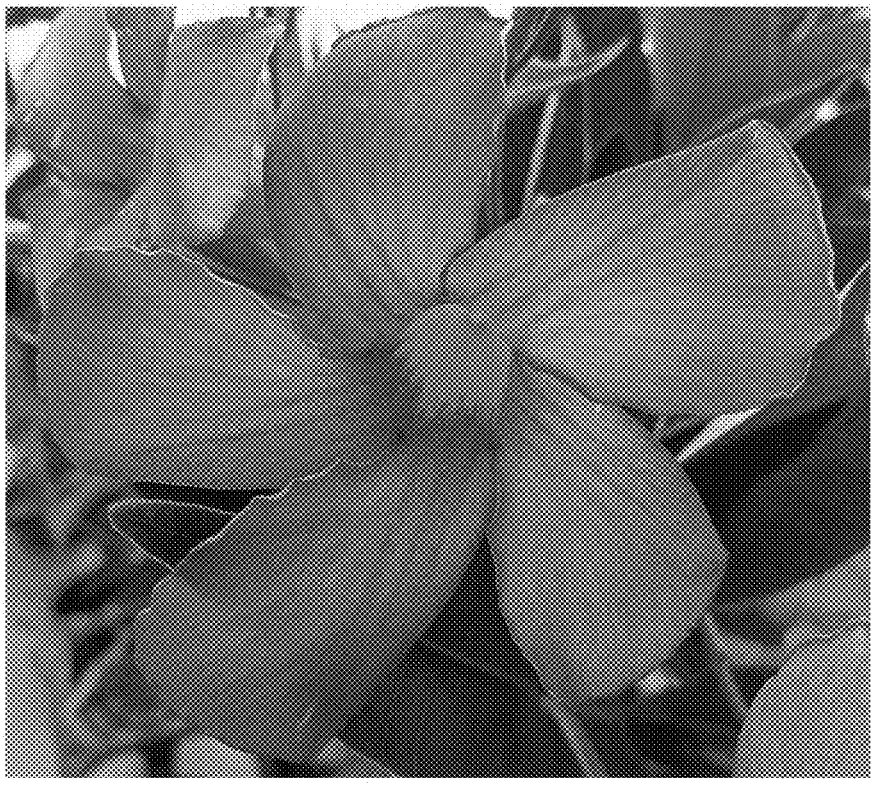

The photograph on the second sheet (FIG. 2) is a close-up view of a typical flower of 'Sunpa 424'.

DETAILED BOTANICAL DESCRIPTION

The aforementioned photographs and following observations, measurements and values describe plants grown during the late summer in 15-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were six months from planting rooted young plants when the photographs and the detailed description were taken. In the following description, color references are made to The Royal Horticultural Society Colour Chart, 2015 Edition, except where general terms of ordinary dictionary significance are used.

Botanical classification: *Mandevilla hybrida* 'Sunpa 424'.

Parentage:

*Female, or seed, parent.*—Proprietary selection of *Mandevilla hybrida* identified as code number 12M162, not patented.

*Male, or pollen, parent.*—Proprietary selection of *Mandevilla hybrida* identified as code number 10M490, not patented.

Propagation:

*Type.*—By terminal vegetative cuttings.

*Time to initiate roots, summer and winter.*—About two weeks at temperatures about 23° C. to 25° C.

*Time to produce a rooted young plant, summer and winter.*—About five to six weeks at temperatures about 23° C. to 25° C.

*Root description.*—Fibrous; typically light brown in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Climbing plant habit; vigorous growth habit; freely basal branching habit; suitable for hanging baskets and garden plantings.

*Plant height.*—About 148 cm.

*Plant diameter.*—About 52 cm.

*Lateral branch description.*—Length: About 75 cm. Diameter: About 4 mm. Internode length: About 3.6 cm. Strength: Strong, flexible. Aspect: Mostly upright. Texture: Sparsely pubescent. Color, developing: Close to 144A. Color, fully developed: Close to 152B.

Leaf description:

*Arrangement and quantity.*—Decussate, simple; dense, about 17 leaves per lateral branch.

*Length.*—About 10.6 cm.

*Width.*—About 4.4 cm.

*Shape.*—Elliptic; incurving.

*Apex.*—Acuminate.

*Base.*—Cordate.

*Margin.*—Entire; slightly undulate.

*Texture and luster, upper and lower surfaces.*—Smooth, glabrous; moderately glossy.

*Venation pattern.*—Pinnate, reticulate.

*Color.*—Developing leaves, upper surface: Close to NN137A. Developing leaves, lower surface: Close to 138A. Fully expanded leaves, upper surface: Close to NN137A; venation, close to 144A. Fully expanded leaves, lower surface: Close to 144A; venation, close to 145B.

*Petioles.*—Length: About 1.3 cm. Diameter: About 2.1 mm. Texture, upper and lower surfaces: Sparsely pubescent. Color, upper and lower surfaces: Close to 144A.

Flower description:

*Flower type and habit.*—Single-type flowers; flowers face mostly upright to outwardly; freely flowering habit with about nine flowers per axil and about 124 flowers developing per plant.

*Natural flowering season.*—Plants begin flowering about six weeks after planting rooted young plants; long flowering period, plants flower continuously from summer until late autumn in Japan.

*Flower longevity on the plant.*—About seven to ten days; flowers not persistent.

*Fragrance.*—None detected.

*Flower buds.*—Height: About 6.2 cm. Diameter: About 1.2 cm. Shape: Rhombic. Color: Close to 62A, 150D and 145B.

*Flowers.*—Appearance: Single-type, five petals in a single whorl; flowers salverform with campanulate throats. Diameter: About 7.5 cm. Depth (length): About 5.8 cm.

*Corolla.*—Quantity and arrangement: Five petals fused towards the base into an elongated throat and tube; petal lobes free and not imbricate. Petal lobe length:

About 3.4 cm. Petal lobe width: About 2.5 cm. Throat diameter, distally: About 1.3 cm. Throat diameter, proximally: About 6.2 mm. Throat length: About 2.7 cm. Tube length: About 1.6 cm. Tube diameter, proximally: About 2.6 mm. Petal lobe shape: Spatulate, strongly asymmetrical. Petal lobe apex: Acute. Petal lobe margin: Entire; slightly undulate and slightly recurving. Petal lobe texture and luster, upper and lower surfaces: Smooth, glabrous; matte. Throat texture: Smooth, glabrous. Tube texture: Smooth, glabrous. Color: Petal lobe, when opening, upper surface: Close to 63D. Petal lobe, when opening, lower surface: Close to 63C, 63B and 63A. Petal lobe, fully opened, upper surface: Close to 63A; venation, close to 63A; color does not change with subsequent development. Petal lobe, fully opened, lower surface: Close to 63B and 63A; venation, similar to lamina colors; colors do not change with subsequent development. Throat, inner surface: Distally, close to 63B and 15C; proximally, close to 15A; venation, close to 63B. Throat, outer surface: Distally, close to 63B; proximally, close to 63B and 145C; venation, close to 145B. Tube: Close to 145C and 145B; venation, similar to lamina colors.

*Calyx*.—Quantity and arrangement: Five sepals arranged in a single whorl, fused at the base into a tube; calyx, star-shaped. Sepal length: About 6.2 mm. Sepal width: About 1.8 mm. Sepal shape: Lanceolate. Sepal apex: Acuminate. Sepal margin: Entire. Sepal texture, upper and lower surfaces: Smooth, glabrous. Sepal color, upper surface: Distally, close to 58A; proximally, close to 145B. Sepal color, lower surface: Distally, close to 61B; proximally, close to 138B.

*Peduncles*.—Length: About 2.2 cm. Diameter: About 2 mm. Texture: Sparsely pubescent. Aspect: Upright to outwardly. Color: Close to 144B.

*Pedicels*.—Length: About 1.5 cm. Diameter: About 2.1 mm. Texture: Smooth, glabrous. Aspect: Upright to outwardly. Color: Close to 144B.

*Reproductive organs*.—Stamens: Quantity: Five. Anther size: About 1.4 mm by 6.3 mm. Anther shape: Lanceolate. Anther color: Close to 10A. Amount of pollen: Sparse. Pistils: Quantity: Typically one. Pistil length: About 1.8 cm. Style color: Close to 145C. Stigma shape: Conical. Stigma color: Close to 145A. Ovary color: Close to 145A.

*Seeds and fruits*.—To date, seed and fruit development have not been observed on plants of the new *Mandevilla*.

Pathogen & pest resistance: To date, plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C. and to be suitable for USDA Hardiness Zones 11 and 12.

It is claimed:

1. A new and distinct *Mandevilla* plant named 'Sunpa 424' as herein illustrated and described.

* * * * *